United States Patent
Bonmassar et al.

(10) Patent No.: US 9,486,168 B2
(45) Date of Patent: Nov. 8, 2016

(54) IMPLANTABLE ELECTRODE SYSTEM

(71) Applicants: Giorgio Bonmassar, Lexington, MA (US); Alexandra Golby, Boston, MA (US)

(72) Inventors: Giorgio Bonmassar, Lexington, MA (US); Alexandra Golby, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 66 days.

(21) Appl. No.: 14/396,529

(22) PCT Filed: Apr. 26, 2013

(86) PCT No.: PCT/US2013/038340
§ 371 (c)(1),
(2) Date: Oct. 23, 2014

(87) PCT Pub. No.: WO2013/163503
PCT Pub. Date: Oct. 31, 2013

(65) Prior Publication Data
US 2015/0099959 A1 Apr. 9, 2015

Related U.S. Application Data

(60) Provisional application No. 61/639,392, filed on Apr. 27, 2012.

(51) Int. Cl.
*A61B 5/0478* (2006.01)
*A61N 1/05* (2006.01)
(Continued)

(52) U.S. Cl.
CPC ........... *A61B 5/6846* (2013.01); *A61B 5/0478* (2013.01); *A61B 5/055* (2013.01);
(Continued)

(58) Field of Classification Search
CPC .............. A61B 5/0478; A61B 5/6846; A61N 1/0529; A61N 1/0531; A61N 1/0534
USPC .................................. 600/377, 378; 607/116
See application file for complete search history.

(56) References Cited

U.S. PATENT DOCUMENTS 6,994,671 B2 * 2/2006 Oka ................... G01N 33/5088
600/300
7,146,221 B2 * 12/2006 Krulevitch ........... A61N 1/0543
607/116

(Continued)

FOREIGN PATENT DOCUMENTS

EP 1 790 380 A1 5/2007
RU 2423154 C2 7/2011

OTHER PUBLICATIONS

International Search Report and Written Opinion under date of mailing of Sep. 26, 2013 in connection with PCT/US2013/038340.

*Primary Examiner* — Lee S Cohen
(74) *Attorney, Agent, or Firm* — Quarles & Brady LLP

(57) ABSTRACT

An electrode array (10) is configured for implantation into a subject. The electrode array (10) includes an organic substrate material (12) configured to be implanted into an in vivo environment and to optionally dissolve after implantation into the in vivo environment and be absorbed by the in vivo environment, and an electrode (14) mounted to the organic substrate material (12) and configured to acquire signals generated by the in vivo environment. The electrode array (10) includes a connection pad (20) mounted to the organic substrate (12), and a conductive trace (16) formed between the electrode (14) and the connection pad (2). The conductive trace (16) includes a conductive ink that is MRI-compatible.

12 Claims, 8 Drawing Sheets

(51) Int. Cl.
*A61B 5/00* (2006.01)
*A61B 5/055* (2006.01)
*A61N 1/08* (2006.01)

(52) U.S. Cl.
CPC .......... *A61B 5/6868* (2013.01); *A61N 1/0529* (2013.01); *A61N 1/0531* (2013.01); *A61N 1/0534* (2013.01); *A61B 2562/046* (2013.01); *A61N 2001/086* (2013.01); *Y10T 29/49155* (2015.01)

(56) References Cited

U.S. PATENT DOCUMENTS

| | | | |
|---|---|---|---|
| 7,689,260 B2* | 3/2010 | Finch | A61N 1/0529 600/378 |
| 8,306,632 B2* | 11/2012 | Schouenborg | A61N 1/0529 607/117 |
| 8,666,471 B2* | 3/2014 | Rogers | A61B 5/05 600/373 |
| 2010/0229384 A1 | 9/2010 | Krulevitch et al. | |

* cited by examiner

IMPLANTABLE ELECTRODE SYSTEM

CROSS-REFERENCE TO RELATED APPLICATIONS

This application represents the national stage entry of PCT International Application No. PCT/US2013/038340 filed Apr. 26, 2013 and claims priority to U.S. Provisional Patent Application 61/639,392 filed on Apr. 27, 2012, both of which are hereby incorporated herein by reference for all purposes.

STATEMENT REGARDING FEDERALLY SPONSORED RESEARCH

This invention was made with government support awarded by the Department of Defense via CIMIT.

BACKGROUND OF THE INVENTION

The field of the invention is systems and methods for an implantable electrode. More particularly, the invention relates to an electrode comprising a grid or array suitable for use in implanted applications including, for example, intracranial applications.

In patients requiring brain surgery, intracranial electrocortical recording and stimulation can provide unique knowledge about a patient's functional brain anatomy. Electrocortical stimulation (ECS) allows for the investigation of brain function by causing a temporary disruption or activation of function. After the electrodes are placed in or on the brain, recording and stimulating can take place intra-operatively or extraoperatively. This electrophysiologic mapping helps doctors to infer the role of those brain areas in neurologic function. This approach is commonly used, for example, in the treatment of medically refractory epilepsy, functional disorders and brain tumors. However, it can be difficult to integrate the results of subdural recordings made during ECS with other brain mapping modalities, particularly functional magnetic resonance imaging (fMRI).

The ability to integrate imaging and electrophysiological information with simultaneous intracranial or subdural electrocortical recording/stimulation and fMRI may offer insight for cognitive and systems neuroscience as well as for clinical neurology, particularly for patients with epilepsy or functional disorders. Unfortunately, standard intracranial electrodes cause significant artifacts in MRI images, and concern about risks such as cortical heating have generally precluded obtaining MRI in patients with implanted electrodes. In the case of cortical heating, the leads or other conductive structures of some electrodes operate as antennas, focusing radio frequency (RF) electromagnetic waves and causing localized heating, which may result in injury. In addition to heating concerns, the structure of existing electrodes can cause a large increase (e.g., 100-fold) in the strength of the magnetic field near the electrode's conductive components creating inhomogeneities of the $B_0$ field as well as artifacts due to the electrode's density. For imaging, this electromagnetic interference can cause disturbances to an MRI scanner's $B_1$ field, an electromagnetic field used for imaging. The metal in the electrodes could also generate artifacts in other imaging systems, such as streaks that degrade the image quality of computed tomography (CT)—this is particularly problematic as the artifacts are generated at the location being examined—the location of interest from which data is being collected. These concerns have prevented the concurrent use of ECS and related technologies in MRI-guided surgeries, reducing the overall effectiveness of ECS.

Conventional intracranial electrodes also present a number of potential post-operative complications including epidural hematoma, subdural hematoma, significant brain edema, brain swelling, infection, and neurological disorders (e.g., transient aphasia, deficits, or status epilepticus). Short term implantation of intracranial electrodes is often used in the evaluation of patients for epilepsy surgery, but this approach is often limited due to these risks.

Increasingly, the option of chronic implantation of electrodes into the central or peripheral nervous system to record or stimulate, or do both in an open or a closed loop system offers therapeutic options for many neurologic diseases. However, the inability to obtain standard MRI in such patients after placement of the devices introduces a consequent risk, moreover, the bulkiness of the hardware with its associated complications makes chronic implantation problematic.

SUMMARY OF THE INVENTION

In one implementation, the present invention is an electrode array configured for implantation into a subject. The electrode array includes an organic substrate material configured to be implanted into an in vivo environment and to dissolve after implantation into the in vivo environment and be absorbed by the in vivo environment, and an electrode mounted to the organic substrate material and configured to acquire signals generated by the in vivo environment. The electrode array includes a connection pad mounted to the organic substrate, and a conductive trace formed between the electrode and the connection pad. The conductive trace includes a conductive ink.

In another implementation, the present invention is a method of manufacturing an electrode array, comprising mounting an electrode to an organic substrate configured to be implanted into an in vivo environment. The electrode is configured to acquire signals generated by the in vivo environment. The method including forming, by polymer thick film deposition, a conductive trace on the organic substrate, the conductive trace being electrically connected to the electrode, and forming a connection pad on the organic substrate, the connection pad being electrically connected to the conductive trace.

DETAILED DESCRIPTION OF THE INVENTION

This disclosure relates to systems and methods for an implantable electrode. More particularly, the invention relates to an electrode comprising a strip, grid or array suitable for use in implanted applications including, for example, intracranial applications.

Figure 1:
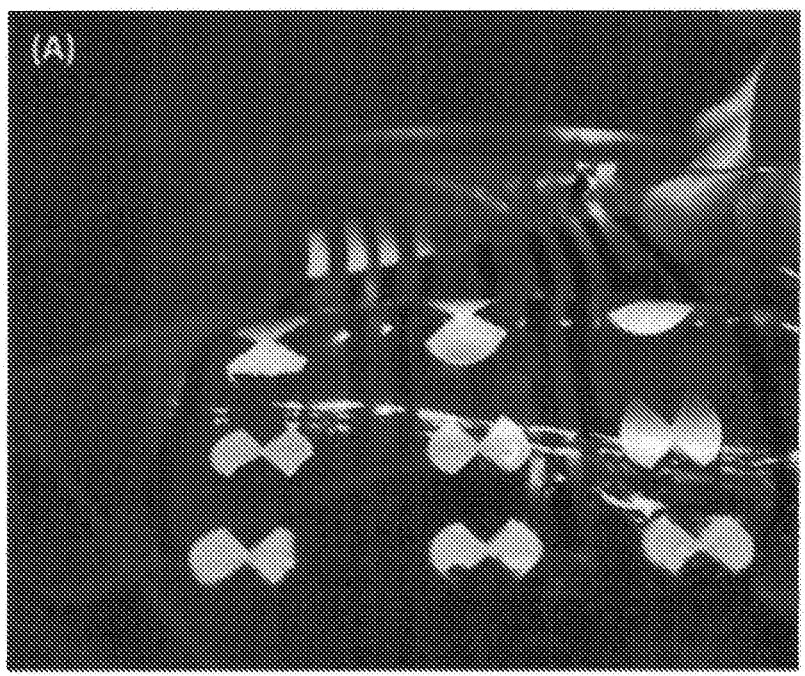
FIG. 1 shows an example electrode array constructed in accordance with the present disclosure.

The present electrode array is absorbable, flexible, stretchable, and MRI-compatible. FIG. 1 shows an example electrode array constructed in accordance with the present disclosure. The electrode array includes a number of electrodes formed over a thin flexible substrate. A conductive ink is deposited and cured over the substrate to form thin electrical interconnects between the electrode array and external systems. A polymeric surface may coat the electrode to maximally encourage cell attachment compared to conventional metallic electrodes, such as platinum Iridium, stainless steel and gold, which have minimal interaction with tissue.

The present electrode array is suitable for in vivo implantation into a patient (where in vivo implantation means implantation into a living organism). When implanted into a patient (e.g., over a patient's brain), the thin flexible substrate of the electrode array allows the electrodes to contact and lay flat against internal surfaces of the patient's body (e.g., the convoluted brain surface), placing the electrodes in close proximity to those surfaces. When the electrode array is implanted subdurally, because the electrodes are positioned close to the brain surface, the electrodes of the present electrode array cause less distortion to the brain. These characteristics allow for longer term use of the electrodes and allow for the development of improved brain-machine interfaces. When installed in other sites, the flexible substrate allows the electrode array to conform to any target surface, such as when the electrode array is positioned about an external surface of an organ, bone, or other body structure. These characteristics can reduce actual, physical distortion of the brain structure leading to more accurate imaging.

Over time, the electrode array's substrate is absorbed by the patient's body, leaving only the thin structures of the electrodes and thin conductive traces remaining in the patient. In one implementation, the thickness of the electrodes and conductive traces are nanoscale (e.g., on the order of a few microns). By allowing the substrate to be absorbed, the present electrode array provides a mechanism for implanting an extremely thin electrode array within a patient. Because the electrode array, with substrate absorbed, has a thin profile, the array, even in its entirety, is for the patient and can safely be used in conjunction with a number of imaging technologies, including, for example, MRI.

When implanted over a patient's brain, the electrode array can be used for functional imaging of underlying neural networks elicited by each electrode at the individual patient level. By minimizing the difficulties associated with conventional electrode systems, the present electrode array is compatible with a number of different imaging systems. As a result, procedures such as simultaneous subdural electrocortical recording/stimulation and fMRI can be performed using the present electrode array without an increased risk to the patient and without creating distortions in the resulting imaging. The present electrode array is also useful in additional applications involving the monitoring or delivery of electronic signals from or to the spinal cord, retina as well as other nerve applications (e.g. vagal nerve, or peripheral nerve applications).

Figure 2:
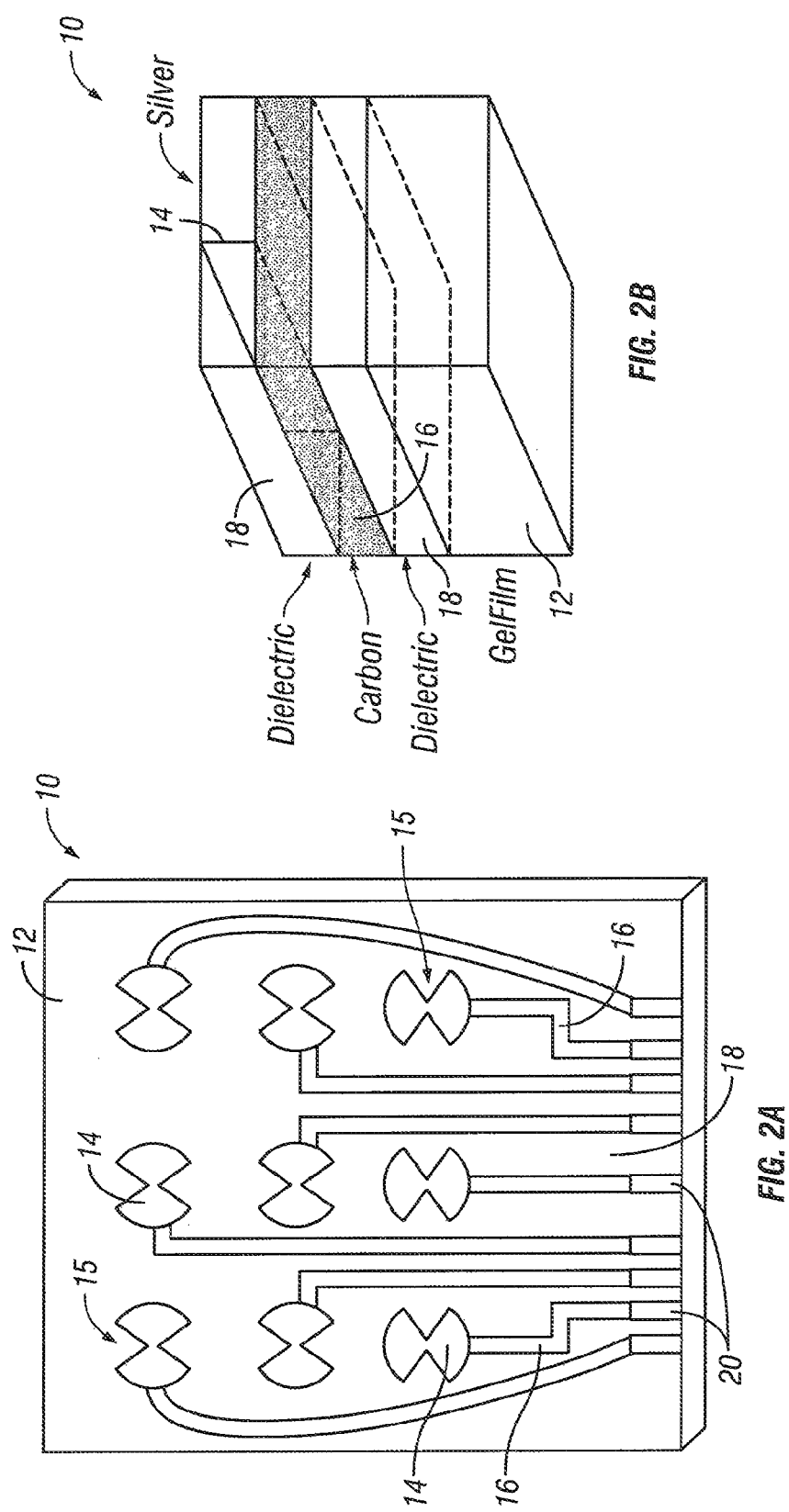
FIG. 2A is a top view of an electrode array in accordance with this disclosure.
FIG. 2B shows a cross-section of a portion of the electrode array shown in FIG. 2A.

FIG. 2A is a top view of an electrode array in accordance with this disclosure. FIG. 2B shows a cross-section of a portion of the electrode array shown in FIG. 2A. When implanted intracranially, the electrodes of the array are generally positioned in contact with the pial plane of the brain paranchyma so that the purely organic substrate surface of the electrode array is in contact with the dura and faces the cranium.

Electrode array 10 includes a substrate 12. Substrate 12 is an organic substrate that can be absorbed by a patient's body after electrode array 10 is implanted. Example substrates include an absorbable gelatin film (e.g., Gelfilm by Pharmacia and Upjohn Co, Division of Pfizer Inc, NY), which is commonly used in neurosurgery as a dural substitute. This gelatin film can be manufactured from denaturated collagen that, when dry, has a texture and appearance similar to cellophane. When moistened, the film becomes rubbery allowing the film to be manipulated to contour to non-planar surfaces found within the patient's body at the implant site. When implanted into a patient, substrate 12 is configured to dissolve and be absorbed by the patient's body. In some implementations, substrate 12 may be impregnated with a number of different therapeutic substances, medications, or chemicals, such as steroids to decrease inflammation or anticonvulsants so as to deliver medications to the patient as substrate 12 is absorbed over time.

Substrate 12 may alternatively include other bio-absorbable or biodegradable polymers with hydrolyzable chemical bonds (i.e., water can break the chemical bonds in a timely fashion, such as within hours, days, months etc.). Example polymers include polylactic acid (PLA), polyglycolic acid (PGA), copolymers (PLA/PGA), polycaprolactone (PCL), poly(hydroxyalkanoate)s and polyesters. Other suitable bio degradable polymers for substrate 12 can include natural polymers, such as collagen, gelatin, elastin, silk and polysaccharide (e.g., starch and cellulose). Some of these polymers can be transformed into fibers that are then spun together and woven into a cloth or a biomedical textile, which can serve as substrate 12 for electrode array 10.

A number of electrodes 14 are formed over a surface of substrate 12. Electrodes 14 include a conductive material, such as gold, gold, platinum, and the like. In one implementation, the electrodes include gold flakes or nanoparticles disposed within a polymer binder material. To improve charge transfer (and reduce the amount of power required for operation), the surface of electrodes 14 may have a roughened or porous surface. As shown in FIG. 2A, in one implementation, electrodes 14 are fabricated in the shape of circular pads of conductive material with a number of removed wedges 15. The removed portions of electrodes 14 interrupt the circular symmetry of the electrodes and act to minimize the formation of eddy currents within the structure of electrodes 14. By minimizing the formation of eddy currents, electromagnetic interference and potential heating caused by electrodes 14 is reduced. Electrodes 14 can be used to stimulate a patient (e.g., by the delivery of an electrical stimulating signal), or can be used to take measurements from the patient's body by detecting electrophysiological signals generated therein. The electrodes may generally take any size and shape. In one implementation, the electrodes have a geometry of about 0.5 mm².

Electrodes 14 are connected to an interconnected network comprising a number of traces 16. Traces 16 are formed from a conductive material, such as a carbon-based conductive ink and are flexible. As a result, traces 16 can stretch and bend as substrate 12 is manipulated to conform to surfaces within the patient's body when electrode array 10 is implanted. In one implementation, the conductive inks include polymeric binder material provide for adhesion of the ink (in general, the conductive inks comprise a dielectric binder that includes a conductive nanoparticle filler). In one implementation, traces 16 include a mixture of one or more conductive inks, generally carbon and gold. Alternatively, traces 16 include a mixture of carbon and gold or platinum inks or a mixture of organic conductive inks (e.g., Sigma-Aldrich 719102) mixed with gold and/or platinum nanoparticles to increase conductivity. Other metals that can be used to increase conductivity include non-ferromagnetic, implantable grade metals, such as aluminum, tungsten, Tantalum, and various biocompatible alloys including titanium alloys, cobalt-chromium alloys, and stainless steels.

One or more layers of dielectric material 18 are formed over substrate 12 to electrically isolate traces 16 from one another. Dielectric 18 may also provide an adhesive function for attaching both electrodes 14 and traces 16 to substrate 12 and may provide physical support and protection to electrodes 14 and traces 16.

Finally, a number of connection pads 20 are formed over substrate 12. Connection pads 20 are in electrical connection with traces 16 which are, in turn, electrically connected to electrodes 14. Connection pads 20 allow for the electrical interconnection of electrodes 14 of electrode array 10 with external systems and devices.

When electrode array 10 is implanted within a patient, a number of different techniques can be used to form an electrical connection between electrode array 10 and an external stimulation or measurement device. For example, in cases where the electrode array is installed for an extended period of time over a patient's brain, a port can be formed through the patient's skin and skull, and wires can be passed through the port to form the appropriate connections. Alternatively, it is possible to tunnel a wire under the patient's skin from one or more of connection pads 20 to a suitable location (e.g., near the user's clavicle) where an appropriate stimulator or sensor system can be installed. Finally, wireless connections can be established between an implanted electrode array and external electronic circuitry.

In one implementation, electrode array 10 is manufactured using Polymer Thick Film (PTF) deposition on top of an organic substrate (PTFOS). PTFOS is a technique that allows the deposition of conductive materials, such as conductive inks over an organic substrate (e.g., substrate 12 shown in FIGS. 2A and 2B). As discussed above, one suitable substrate includes an absorbable gelatin film. The gelatin film material is manufactured from denaturized collagen and, after being implanted into a patient, is absorbed within a few months. The substrate can be used as a temporary replacement for a number of tissues in the body. In one example, the substrate is used in place of a portion of the patient's dura mater when the electrode array is implanted over the patient's brain (more precisely, the gelfilm is used to help separate tissue layers and provide a scaffold for tissue ingrowth). In one implementation, the thickness of the gelatin film substrate is approximately 75 micrometers, though other films (e.g., having thicknesses of 1-2 millimeters) can be used.

To form the traces of the electrode array, one or more layers of dielectric 18 are built-up over the surface of substrate 12. The dielectric can include any non-conductive material suitable for deposition using PTFOS processes and forms an appropriate attachment point for the conductive traces. The dielectric (and other components of the electrode array) can be deposited using a number of deposition techniques including pad printing, silk screen printing, inkjet printing, pen writing or syringe dispensing, and photolithography, which allows for the printing of structure on the scale of microns. In some cases, the organic inks require spin-coating. The dielectric is waterproof, otherwise the insulating properties of the dielectric could become compromised over time. While present in the patient, the dielectric coating should not exhibit an increase in leakage current.

In some implementations, structures other than traces may be built-up over the surface of substrate 12. For example, using the described deposition processes (e.g., pad printing, silk screen printing, inkjet printing, pen writing, and photolithography, which can allow for the printing of structure on the scale of microns) structures such as antennas, logic circuits, and the like, may be formed over the surface and interconnected with one or more of electrodes 14 and/or connection pads 20. For example, in some implementations, structures such as radio-frequency identification (RFID) tags may be formed over substrate 12.

Biocompatible dielectric binders include: Polyimides, silicones, poly(ethylene), poly (vinyl chloride), polyurethanes, polylactides, elastomer gels, urethanes, block copolymers, liquid crystal polymers, and polymer brush. In general the binders include standard thermoplastic binders, thermosets and radiation curable systems that are biocompatible.

Conductive inks are then deposited over dielectric 18 to form traces 16 using a suitable deposition process, such as PTFOS. The conductive inks include powdered or flaked particles of conductive materials, such as gold or carbon-like materials, suspended in an appropriate binder material. Other metals that can be used to increase conductivity include non-ferromagnetic, implantable grade metals, such as aluminum, tungsten, Tantalum, and various biocompatible alloys including titanium alloys, cobalt-chromium alloys, and stainless steels. In some cases, the inks include use nanoparticle ink technologies. After the ink is deposited to form the traces, the ink is put through a curing or annealing process to prepare the ink for use. In one implementation, the depth or thickness of the traces formed by the conductive ink is from 5 to 10 micrometers. The traces can be multilayered with vias or with bridging PTF inks to connect one layer to the other. The sensors and leads can be used for Transcranial Magnetic Stimulation (TMS).

Once cured, traces 16 remain flexible, allowing traces 16 to bend, flex and/or stretch with substrate 12 as substrate 12 is manipulated to meet the contours of the surface upon which electrode array 10 is positioned. This flexibility of traces 16 (and, potentially, of other structures) of the present electrode array can reduce strain and damage that may result in contacted tissue that is commonly observed in proximity to conventional, and stiffer, electrode structures. In conventional electrodes, for example, the increased stiffness with respect to the surrounding tissue induces strain and local electrode micromotion produces an inflammatory response that may adversely affect tissue health.

In one example implementation of electrode array 10 (see, for example, the array depicted in FIG. 1), the resistances of the nine conductive traces/electrode combinations at 100 Hz are given in Table 1, below.

TABLE 1

Resistivity @100 Hz of each electrods/lead. Numbering started top left and continued column wise.

| | ELEC 1 | ELEC 2 | ELEC 3 | ELEC 4 | ELEC 5 | ELEC 6 | ELEC 7 | ELEC 8 | ELEC 9 |
|---|---|---|---|---|---|---|---|---|---|
| R ($\Omega$) | 3.1k | 1.4k | 1.9k | 2.7k | 1.4k | 2.8k | 2.4k | 1.8k | 4.0k (*) |

(*) Elec 9 was retested after 3 months in saline solution and exhibited a 5.1 k$\Omega$ resistivity.

Electrodes 14 are deposited onto substrate 12 using any suitable deposition method. Electrodes 14, for example, may comprise prefabricated structures formed of conductive metals that are fastened to substrate 12 and connected to traces 16 using a conductive adhesive. Alternatively, electrodes 14 can be formed at the same time as traces 16 as part of the same conductive ink deposition process. Electrodes 14 may also be formed in a deposition process that is separate from the process that forms traces 16 (for example, if electrodes 14 include a different material than that of traces 16).

In some implementations, after formation of the inks and deposition of electrodes 14, additional layers of dielectric material are formed over traces 16 to provide environmental protection and electrical isolation for each of traces 16. Additionally, after electrode array 10 is implanted and substrate 12 is absorbed by the body, dielectric material provides structural support to each of electrodes 14, traces 16 and connection pads 20. In one implementation, the dielectric layers are approximately 0.075 mm in thickness in dry form.

Generally, the inks and dielectric materials of electrode array 10 are selected so that any necessary curing or annealing processes for each type of material can be performed without damaging the substrate over which the inks and dielectric materials are deposited. Many conductive inks, for example, have curing processes that are not suitable for use in conjunction with organic substrate materials. Additionally, common dielectric materials require curing via ultraviolet light, which could destroy the organic substrate.

Accordingly, in one implementation of the present electrode array, the dielectric and conductive ink materials comprise a thermoplastic binder that binds well with the organic substrate and provides a suitable material over which to deposit the traces. One thermoplastic binder has a curing temperature point of approximately 50 degrees Celsius, which is compatible with most organic substrate materials. Additionally, the thermoplastic binder materials can withstand being subjected to moisture—as will be encountered when the electrode array is implanted within a patient. Other binders, when exposed to moisture, may flake away from the substrate, greatly diminishing the effectiveness of the electrode array and possibly causing injury to the patient.

Connection pads 20 may be formed over substrate 12 using the conductive ink deposition process described above, or any other suitable formation process. The connection pads are formed in accordance with the requirements of the equipment to be coupled to the electrode array. For example, the connection pads may include MRI-compatible connector structures. In one implementation, the connection pads use non-ferromagnetic materials (e.g., Stainless Steel) for a coating layer beneath a platinum layer. The pads may be printed using pure gold highly conductive inks.

In one implementation of the electrode array, the lead traces connecting to the connection pads have variable-resistance along the length of individual sensor leads, with resistance profiles being dictated by specific frequency response attenuation required for imaging device and physiological recording application. Enabling technologies for this implementation include, but are not limited to, carbon flex-circuit printing, gold flex-circuit printing, carbon-gold composite flex-circuit printing, and/or variable resistance carbon weave wires. The wireless electrode lead system may possess impedance profiles tailored to specific MRI field strengths or applications with specific pulse sequences with differing RF characteristics. Further customizations may be made to optimize performance for specific MRI manufacturers and models, specific bore configurations, head coils, and EEG acquisition systems.

The lead wires may be laid out and bound together in such a way as to produce a fixed relative position between sensor wires and reference and ground wires. Groups of electrodes may be partitioned into spatial zones (e.g., "frontal," "occipital," "left or right temporal," etc.), each with an associated fixed relative position layout.

The sensors and leads additionally cause lower temperature increases in the head compared to metallic grids with same MRI-RF input power. The sensors and leads can be safely used in high magnetic fields (e.g., MRI conditional at 7 T) because of the minimal or no use of metals, no torque or translational forces that would tend to align to the strong magnetic field is exerted on the set, display no or extremely small image artifact, MRI image quality remains unaffected, are capable of delivering or measure electrophysiology signals with no additional noise with respect to commercial electrodes, no or very limited induced currents (dB/dt) and no or very limited heating due to the very weak interaction with RF fields generated in the MRI.

The spatial layout of sensors montages within the system can also be optimized to enhance source localization inverse computations, with customizations for particular brain regions and experiment types.

In one implementation, the lead extensions from the electrode array to the stimulator/recording unit implanted in the patient are non-organic and non-absorbable. One suitable material for the lead extensions includes a Liquid Crystal Polymer (LCP). LCP fibers possess unique and important properties, such as: (a) strength for mechanically biostable leads, (b) creep resistance to ensure long life of the chronic implants, (c) abrasion resistance to sustain the repetitive wire linear motion during subject's movement, (d) flex/fold characteristics optimal for bending reliability, (e) minimal moisture absorption for avoiding leaking/corrosion and improving biostability, (f) chemical resistance for biocompatibility, (g) low coefficient of thermal expansion for lead fabrication, (h) high dielectric strength for insulation, important as inks may be deposited on top of the substrate without need of dielectric, (i) cut resistance for avoiding electrical breaks in the implant lead, (j) good retention properties for prolonged implant life, (k) high impact resistance and (l) good shock absorbance for reducing potential neuroprosthetic leads damage during accidents. Offgassing tests show that the material performs well within parameters for this application. LCP also offers decreased UV degradation for resilience to this type of implant sterilization.

Chronically implanted electrodes can provoke an immune reaction. Some research, for example, shows gliosis and spongiosis around the electrode track, which forms an encapsulation layer referred to as the "glial scar". LCP is a biocompatible polymer given that it is inert. LCP is capable of withstanding most chemicals at elevated temperatures, including aromatic or halogenated hydrocarbons, strong acids, bases, ketones, etc. In commercial medical applications, LCP is being used to replace metal in implants (e.g., tibia, femur, clavicle, and hip orthopedic implants, bones screws and plates), and for precision mechanical elements in drug delivery systems.

After electrode array 10 is formed, the electrode array can be implanted into a patient. In one use case, for example, the electrode array can be subdurally implanted over a patient's brain, with the electrode array's substrate and conductive traces conforming to the surface structure of the patient's brain. After the electrode array is implanted, the material comprising the substrate is slowly absorbed by the patient's body. With the substrate material absorbed, only the dielectric material, electrodes, conductive traces, and connection pads of the electrode array remain. In other implementations, the electrode array may be implanted in other sites of the patient in proximity to many different types of tissue for either observation or stimulation of the same. For example, in patients with medically refractory epilepsy who have foci that are not amenable to resection, long term implantation of the present electrode array may be used in combination with closed-loop systems in which detection of epileptiform activity triggers responsive stimulation which aborts the seizure. Other chronic implantation situations may involve brain-machine interfaces for patients with spinal cord or other central nervous system injury, treatment of pain, cochlear implants, bionic eyes, brain-machine interfaces, deep-brain stimulators and pacemakers. Other uses may include the implantation proximate to and stimulation of organs like the bladder and/or tissue, such as striated muscle.

In various implementations, custom electrode arrays may be manufactured in accordance with the present disclosure for particular patients. In that case, the size, shape, and configuration of the electrode array substrate, as well as the arrangements of electrodes, traces, connection pads and other structures, may be designed and configured taking into consideration attributes of the patient and, specifically, the implant site. For example, the number of electrodes on the array could be selected depending upon the particular use of the array (in some cases, electrode arrays having 256 electrodes or more may be manufactured). The organic substrate could be loaded with patient medications for delivery to the tissue proximate the implant site. For example, in the case of brain implants, the substrate may be loaded with medications to potentially bypass the blood-brain barrier and the electrodes could be coated with neurotrophic growth factor to promote neurite outgrowth.

After implantation, the electrical and physical characteristics of the traces do not change with exposure to the chronic implantation conditions within a patient's body, while the substrate material is gradually broken down resulting in complete detachment from the traces while leaving the traces, themselves, intact. In the electrode array, the PTF inks create a chemical bond with the substrate that occurs during crosslinking or other polymerization process. The main characteristic is to have a binder that requires gentle curing, the gelfilm allows temperatures up to 86 degrees Fahrenheit for a short period of time. The present electrode array uses a binder that cures at 50 degrees Celsius.

The PTF material deposition technologies described above are widely used in the electronic manufacturing industry in the production of electronic solid state components. In other implementations, though, other suitable fabrication techniques involve screen printing of conductive inks over an appropriate substrate.

Due to the absorption characteristics of the electrode array's substrate, the thin profile of the electrode array's conductive traces and electrodes, and the shape of the electrodes themselves, the electrode array is well suited to use within the magnetic field generated by various medical imaging devices. Once such imaging system comprises MRI.

Figure 3:
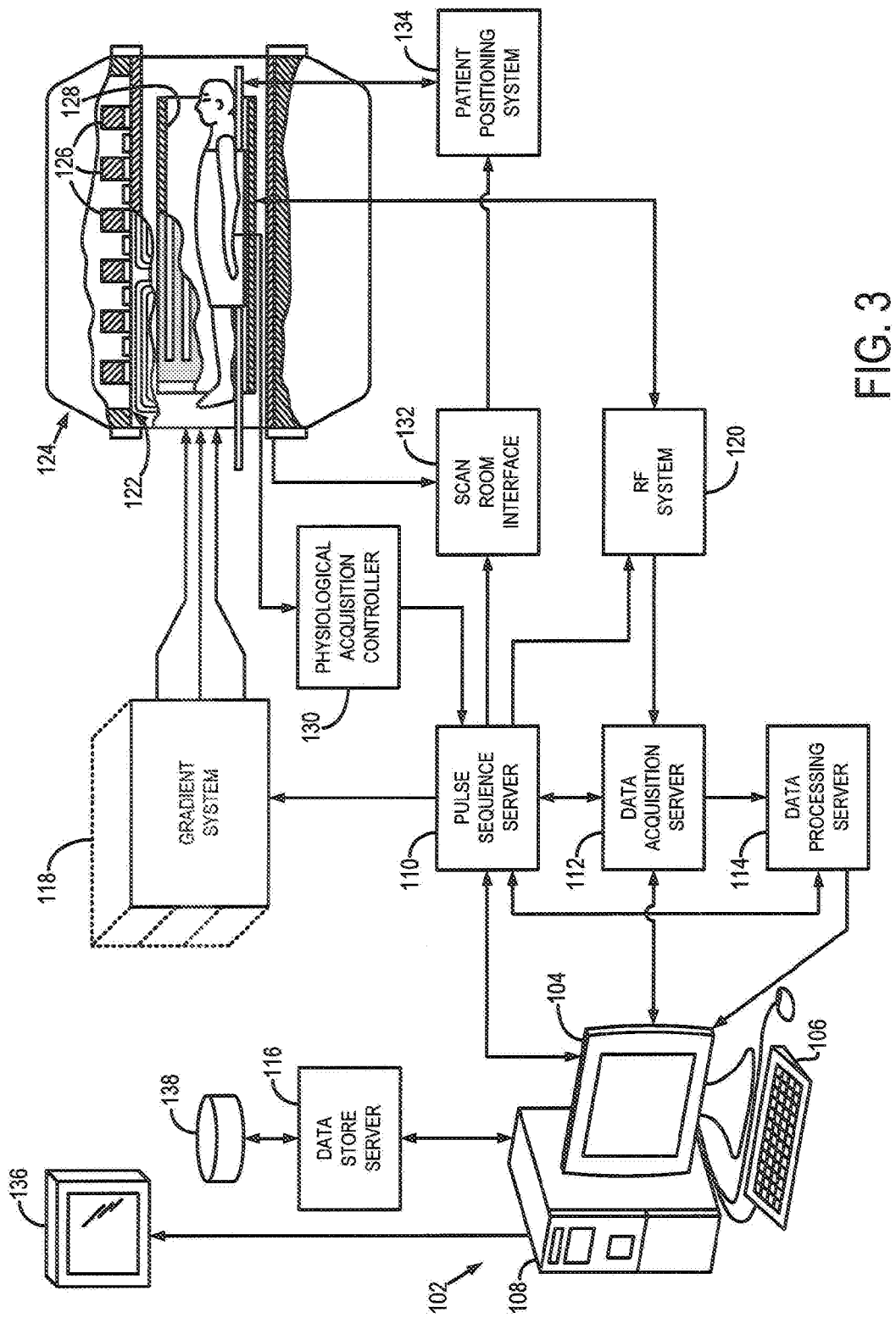
FIG. 3 is a block diagram of an example of a magnetic resonance imaging ("MRI") system.

Referring particularly now to FIG. 3, an example of an MRI system 100 that may be used in conjunction with the present electrode array is illustrated. The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114; and a data store server 116. The workstation 102 and each server 110, 112, 114, and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF waveforms are applied to the RF coil 128, or a separate local coil (not shown in FIG. 3), by the RF system 120 to perform the prescribed magnetic resonance pulse sequence. Responsive MR signals detected by the RF coil 128, or a separate local coil (not shown in FIG. 3), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 3).

The RF system 120 also includes one or more RF receiver channels. Each RF receiver channel includes an RF preamplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \qquad (1);$$

and the phase of the received MR signal may also be determined:

$$\varphi = \tan^{-1}\left(\frac{Q}{I}\right). \quad (2)$$

The pulse sequence server 110 also optionally receives patient data from a physiological acquisition controller 130. The controller 130 may receives signals from a number of different sensors connected to the patient, such as monitoring systems employing the electrode systems of the present invention. In accordance with the present invention, signals from the electrode systems may be coordinated with acquired MRI data and, for example, to be overlayed or integrated with anatomical or physiological, for example, fMRI, images. Additionally or alternatively, the signals received by the controller 130 may include respiratory signals from a bellows, as electrocardiograph ("ECG") signals from a suitable monitoring system, or other signals from monitoring devices. In accordance with the present invention, the controller 130 may receive signals from the aforementioned electrodes or other systems that are then used by the pulse sequence server 110 to synchronize, or "gate," the performance of the scan with the subject's heart beat, respiration, or other biological or physiological occurrences.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. By way of example, the data acquisition server 112 acquires MR data and processes it in real-time to produce information that may be used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 3), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

In addition to using the present electrode array in conjunction with imaging of a patient's brain, the electrode array may also be used in peripheral nerve applications, spinal cord stimulation applications, or retinal applications where the thin profile of the array in conjunction with the flexible and absorbable substrate present numerous benefits to the patient. Conventional implants, for example, exhibit volume and weight that are relatively large, raising the risk that patients develop increased intracranial pressure and attendant complication.

To evaluate the performance of the present electrode array, the MRI properties of the present electrode array can be compared to those of conventional implantable electrode systems as well as the absence of electrodes using a phantom study with clinical MRI sequences. In one example analysis, MRI images were acquired using a 3 T Siemens Trio with a transmit/receive birdcage coil, which is commonly used for imaging patients. A tissue phantom was doped with Gadolinium dissolved in a physiological solution with agarose and had dielectric and T1-weighted properties comparable to those of the human brain.

Figures 4A, 4B, 4C:
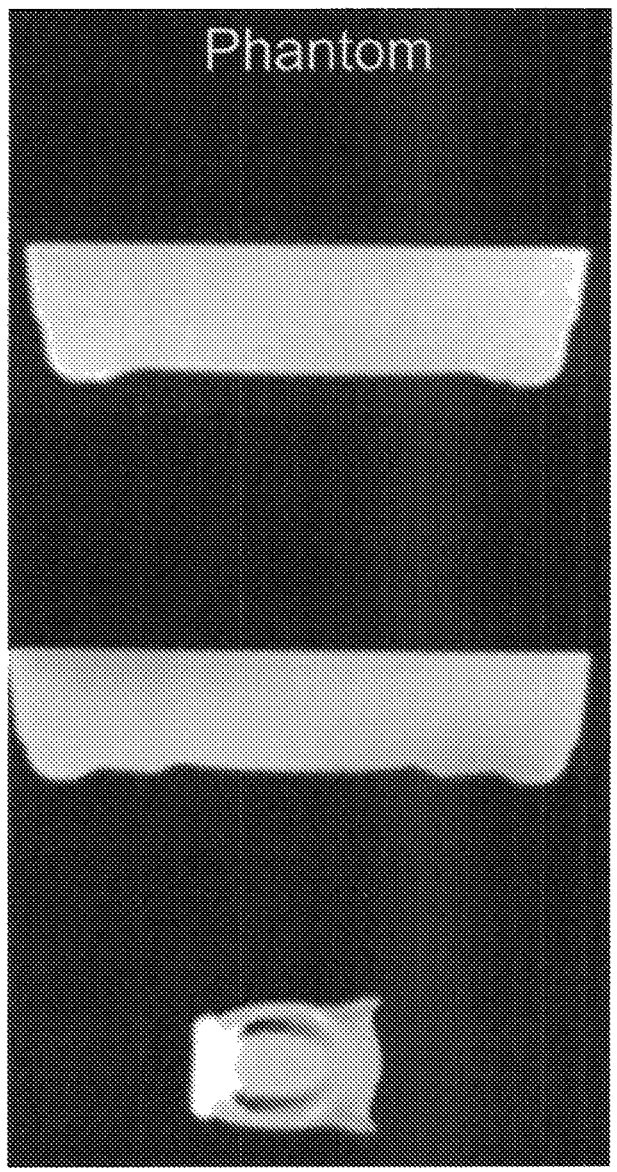
FIGS. 4A-4C are image sets depicting the imaging results when scanning a tissue phantom alone to test for the presence/absence of MRI artifacts.
Figures 5A, 5B, 5C:
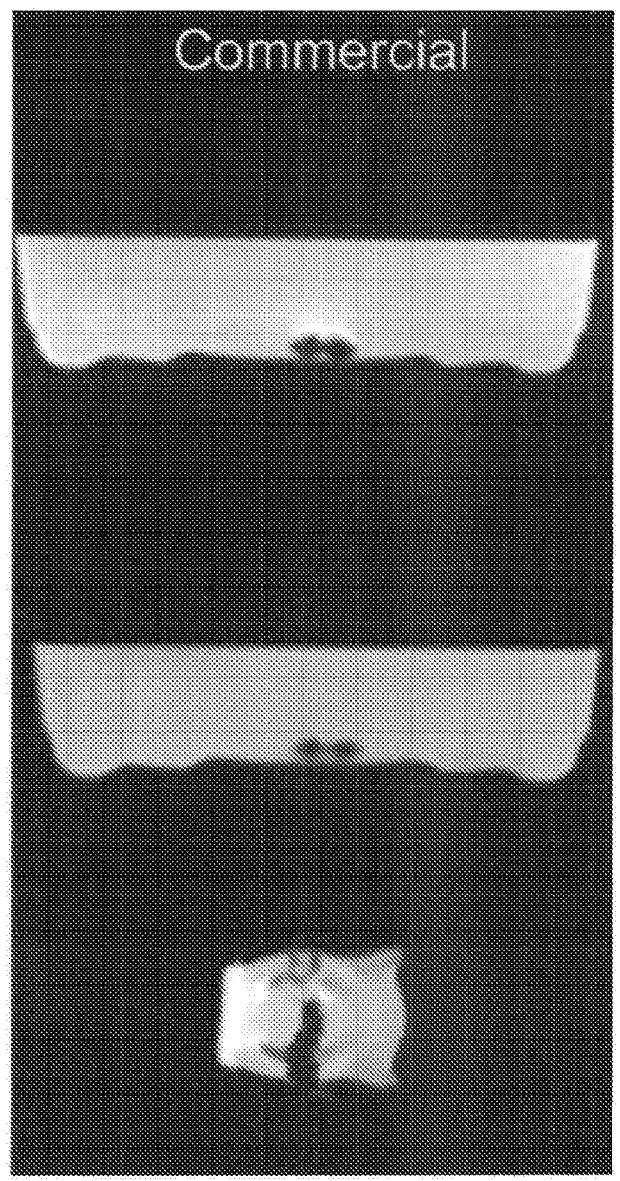
FIGS. 5A-5C are image sets depicting the imaging results when scanning a phantom including a standard electrode set to test for the presence/absence of MRI artifacts.
Figures 6A, 6B, 6C:
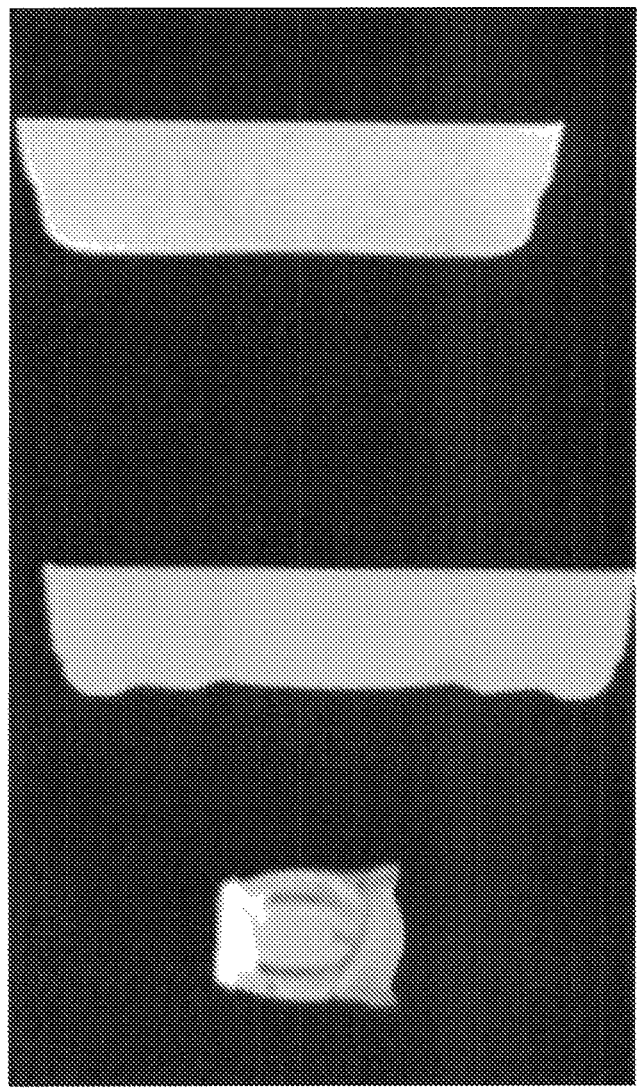
FIGS. 6A-6C are image sets depicting the imaging results when scanning a phantom including the present electrode array to test for the presence/absence of MRI artifacts.

A number of image sets were then captured. The sets include images of the tissue phantom alone (FIG. 4A-4C), the phantom including a standard electrode set (FIG. 5A-5C), and the phantom including the present electrode array (FIG. 6A-6C) to test for the presence/absence of MRI artifacts. FIGS. 4A, 5A, and 6A show T1-weighted images, FIGS. 4B, 5B, and 6B show images of turbo spin echo T2-weighted images and FIGS. 4C, 5C, and 6C show images of T2*Echoplanar Imaging (EPI). FIGS. 4A, 5A, and 6A and FIGS. 4B, 5B, and 6B are taken with MRI sequences commonly used in clinical brain MRI and FIGS. 4C, 5C, and 6C are taken with a typical EPI fMRI sequence.

The artifacts generated by the standard electrode set are visible as a loss of signal with a circular shape generated by the wires in FIGS. 5A and 5B showing the T1 and T2-weighted images. In the case of the present electrode array (FIGS. 6A and 6B) there is no artifact nor loss of signal, but simply a different contrast signal of the Gelfilm substrate compared to just the phantom alone. Similarly for the EPI images (FIGS. 4C, 5C, and 6C), the signal loss was clearly present in the standard 16-channel electrode image (FIG. 5C) and not in the present electrode array image (FIG. 6C) or the image showing the phantom alone (FIG. 4C).

These artifacts extend more broadly than the geometrical dimensions of the electrodes/wires that do not contain water molecules. Although the artifacts may not be visible in conventional MRI, because of the limited resolution often used in clinical scans, the signal loss is exacerbated by the different magnetic properties of metals compared to the surrounding tissue, tending to generate a non-uniform magnetic field around the electrodes/wires. Metals used in implanted electrodes (e.g., gold, platinum, stainless steel, iridium, etc.) have magnetic susceptibility dissimilar to the surrounding tissue therefore causing the observed susceptibility artifact or signal loss.

The present electrode array carries an MRI signal of a biological tissue since the material of the substrate (e.g., a hydrated collagen) has material properties similar to that of body tissue, and the electrode array's electrodes and traces are only a small fraction of a voxel in thickness (e.g., approximately 5 micrometers).

The results depicted in FIGS. 4, 5, and 6 confirm that there was no signal loss with the present electrode array (FIGS. 6A-6C) that contains only a fraction of the metal (i.e., in the case of electrodes, gold with polymers) or no metal at all (i.e., in the case of the traces, carbon-based conductive materials) compared to the wires of a standard implantable electrode set. The metals in standard implantable electrode sets, therefore, have magnetic susceptibility dissimilar to the surrounding tissue, causing the observed susceptibility artifact or signal loss.

The two main sources of MRI artifacts/noise responsible for the observed signal loss are susceptibility artifacts and the $B_0$ field inhomogeneities. In order to understand the relative contribution of these two noise factors, electromagnetic (EM) simulations can be performed. In such studies the amplitude of the $B_1$ field (a much less investigated source of artifacts in the tissue surrounding the implant during a radio frequency (RF) pulse used for imaging in MRI) can be investigated.

Figure 7C:
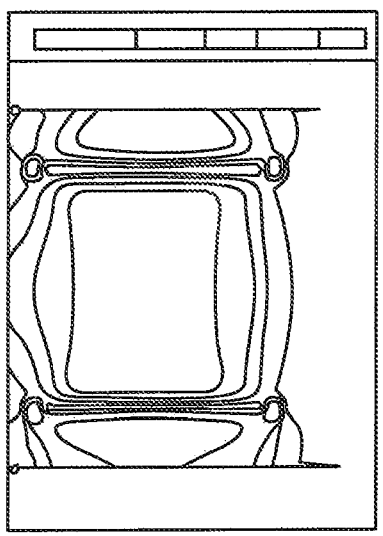
FIGS. 7A-7C show electromagnetic simulation results demonstrating the minimized artifacts of the present electrode array during MRI scanning.
Figure 7B:
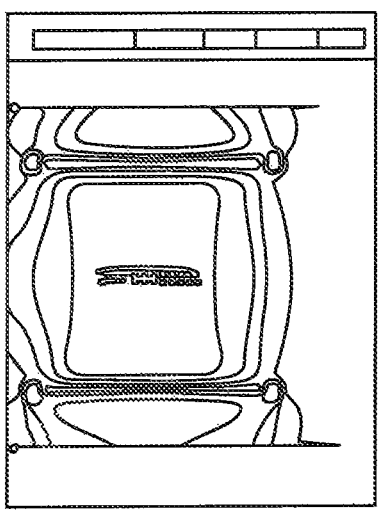
Figure 7A:
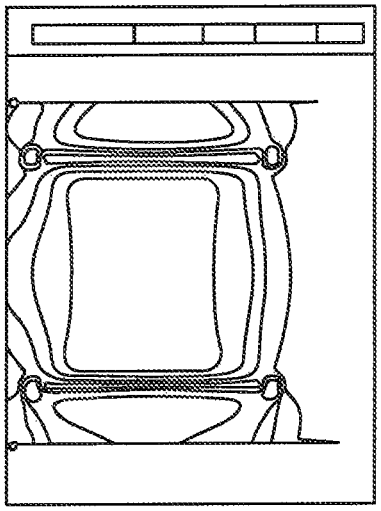

Standard metallic implants with high electrical conductivity implanted inside the human body can cause disturbances in the RF amplitude $B_1$ in the tissue under investigation. These disturbances may become more prominent at 3 T compared to lower MRI field strengths. In order to estimate the $B_1$ field or the magnetic field at the Larmor frequency of interest (127 MHz) electromagnetic Finite Differences Time Domain (FDTD) simulations can be performed in a geometry that models the phantom alone and with the two different types of electrodes (conventional electrodes and the present electrode array). These simulations can closely match the geometry (shape and dimensions) of an actual coil used in MRI acquisitions, of the present electrode array inside the phantom, and of a conventional electrode inside the phantom. The coil used in the simulations is a birdcage coil with 16 spokes that was numerically tuned to match the physical coil, and the two feeds (i.e., with phases of 0 degrees and 90 degrees) set to the voltage amplitudes reported by the scanner. In general, the RF pulse will induce currents in the tissue surrounding the metal implant and the current amplitudes will depend on the wire position, orientation and length inside the coil. In turn, these currents induce a $B_1$ field as shown by the simulations. FIGS. 7A-7C show simulation results demonstrating the minimized artifacts of the present electrode array during MRI scanning.

This simulation predicts a $B_1$ field of approximately $2*10^{-9}$ T for the present electrode array (FIG. 7C) compared to the peak of $4*10^{-9}$ T for the stainless steel or standard set of electrodes (FIG. 7B), or a peak twice as high. Such large peaks in the $B_1$ field caused by the use of conventional electrodes perturb the RF homogeneity near the metal electrode/wires by superposition, where the resulting $B_1$ field will be the superposition of the applied and the induced fields. These large peaks occur only in the $B_1$ field images with stainless steel traces producing the observed halo effect (see, for example, FIG. 5A) whereas no peaks were observed in the images for the present electrode array (see FIG. 6A).

These simulations rely on precise geometrical information of the coil, phantom, and electrodes. However, these simulations also require a precise estimation of all the dielectric constants in the various models. When devices manufactured using PTF are studied with EM simulations and since the binders used in PTF are polar, knowledge of the dielectric properties of the inks and associated binders at the Larmor frequency of interest (~127 MHz) is required. Binders serve to bind the nanoparticles and provide adhesion to the substrate, ensuring the necessary viscosity (or flow) as a requirement for transfer of the ink from the press to the substrate, and contribute to the drying speed and resistance properties of an ink. The problem with polar binders is that these compounds have dispersive dielectric properties, with an electrical conductivity increasing at higher frequencies.

Figure 8:
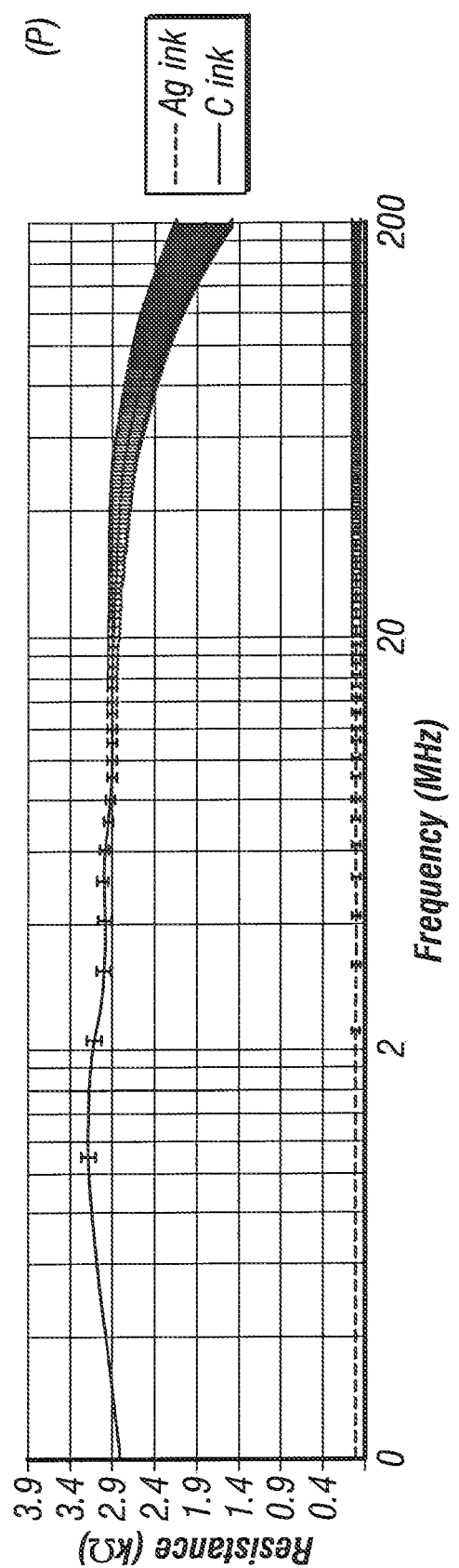
FIG. 8 is a graph showing the resistivity of both the traces and electrodes of the present electrode array at different frequencies.

Since the conductivity of PTF-deposited conductive inks is most commonly specified by the manufacturer at only one frequency (i.e., low or DC) whereas the present electrode array is configured to function at the much higher MRI Larmor frequencies (64 MHz, 128 MHz and 300 MHz), conductivity can be measured to estimate the value to use in the FDTD simulations. FIG. 8 is a graph showing the conductivity of both the traces and electrodes of the present electrode array over a range of frequencies. As demonstrated by FIG. 8, the conductivity of both the traces (e.g., including carbon conductive inks) and the electrodes (e.g., including gold) are quite flat from 100 Hz to 200 MHz, even though there is a dip of 53 percent from the DC value. In all simulations the value of the dielectric properties of the present electrode array was adjusted according to the electrical impedance spectroscopy measurements.

The present electrode array provides for improvements in functional neurosurgery and electrophysiology. Traditional subdural electrode sets still have conductivities larger than $10^5$ $Ohm^{-1}m^{-1}$ necessary to conduct electrical currents for electrocortical stimulation or for ECoG recordings for epileptic foci localization. Such large conductivities can provoke generation of RF-induced eddy currents when patients with grids undergo MRI, potentially generating local heating in the electrodes that may lesion the surrounding tissue.

Most neurosurgeons and neuroradiologists will not perform MRI examinations at 1.5 T or 3 T with implanted subdural grids for fear of electrode displacement, current induction, heating or image artifact in the strong magnetic field. The presented electrode array, as described above, addresses all of these concerns.

The present electrode array may reduce $B_1$ distortion (that can generate heating hazards) as well as the $B_0$ or susceptibility artifacts that can produce signal losses around the components of the electrode array (e.g., the electrodes, traces, etc.). Generally, imaging artifacts vary with the orientation and type of MRI sequence, with T2*epi (or functional MRI) sometimes being the most sensitive to $B_0$ inhomogeneities and T1-weighted, spinecho pulse sequence exhibit usually exhibiting smaller artifacts than those seen with the GRE pulse sequence. $B_1$ and $B_0$ artifacts may change the local MRI flip angle making it relatively difficult in conventional approaches to perform advanced MRI imaging, like MRI thermometry, MR spectroscopy and high-resolution MRI. However, in the present electrode array utilizing PTFOS it can be possible to image patients using such advanced MRI sequences.

The present electrode array can also be used for electrocortical stimulation in a more permanent or chronic settings. In chronic implantations, it may be advantageous to employ biocompatible material, such as platinum, gold, aluminum, tungsten, Tantalum, and various biocompatible alloys including titanium alloys, cobalt-chromium alloys, and stainless steels. Additionally, concerns about risks such as cortical heating have generally precluded performing MRI examinations on patients with implanted electrodes. The present electrode array, as discussed above, minimizes these risks.

The present invention has been described in terms of one or more preferred embodiments, and it should be appreciated that many equivalents, alternatives, variations, and modifications, aside from those expressly stated, are possible and within the scope of the invention.

The invention claimed is:

1. An electrode array configured for implantation into a subject, the electrode array comprising:
   an organic substrate configured to be implanted into an in vivo environment;
   an electrode connected to the organic substrate and configured to acquire signals generated by the in vivo environment, wherein the electrode has an irregular boundary that controls eddy current formation within the electrode;
   a connection pad mounted to the organic substrate; and
   a conductive trace formed between the electrode and the connection pad, the conductive trace including a conductive ink.

2. The electrode array of claim 1, including a thermoplastic binder configured to bind with the organic substrate and configured to receive the conductive trace.

3. The electrode array of claim 1, wherein the electrode is formed of a conductive material deposited within a binder that is substantial invisible in magnetic resonance imaging (MRI).

4. The electrode array of claim 1, including a dielectric formed over a surface of the organic substrate to electrically isolate at least a portion of the conductive trace.

5. The electrode array of claim 1, wherein the organic substrate includes an absorbable gelatin film.

6. The electrode array of claim 5, wherein the absorbable gelatin film has a thickness of about 75 micrometers.

7. The electrode array of claim 1, wherein the conductive trace has a thickness of less than 10 micrometers.

8. The electrode array of claim 1, wherein the conductive trace is formed using Polymer Thick Film (PTF) deposition.

9. The electrode array of claim 1, including a plurality of electrodes mounted to the organic substrate and configured to acquire signals generated by the in vivo environment.

10. The electrode array of claim 1, wherein the organic substrate is configured to dissolve after implantation into the in vivo environment and be absorbed by the in vivo environment.

11. The electrode array of claim 1, wherein the electrode is further configured to deliver an electrical signal to stimulate the subject.

12. The electrode array of claim 1, wherein the electrode comprises a circular pad of conductive material with one or more removed wedges.

* * * * *